Figure 1:
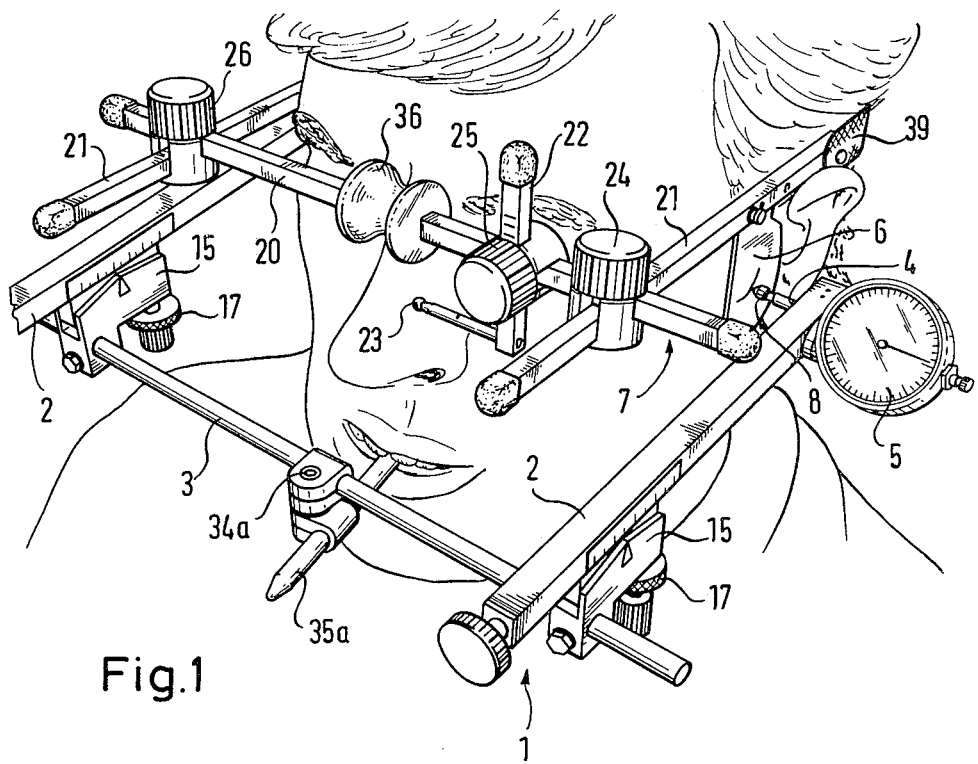

United States Patent [19]

Mack et al.

[11] 4,328,620
[45] May 11, 1982

[54] APPARATUS TO REGISTER THE MOVEMENTS OF THE LOWER JAW WITH REFERENCE TO THE SKULL

[75] Inventors: Heinz Mack, Südl. Auffahrtsallee 64, 8000 München 40, Fed. Rep. of Germany; Günter Singer, München, Fed. Rep. of Germany

[73] Assignee: Heinz Mack, München, Fed. Rep. of Germany

[21] Appl. No.: 87,143

[22] Filed: Oct. 22, 1979

[30] Foreign Application Priority Data

Aug. 28, 1979 [DE] Fed. Rep. of Germany ....... 2937750

[51] Int. Cl.$^3$ .............................................. G01B 3/38
[52] U.S. Cl. ................................ 33/174 D; 33/143 C
[58] Field of Search ......................... 33/174 D, 143 C

[56] References Cited
U.S. PATENT DOCUMENTS

| | | | |
|---|---|---|---|
| 1,662,670 | 3/1928 | Harter | 33/174 D |
| 1,786,915 | 12/1930 | McLean | 33/174 D |
| 3,056,210 | 10/1962 | De Pietro | 33/174 D |
| 3,078,584 | 2/1963 | Cohn | 33/174 D |
| 3,256,523 | 6/1966 | De Pietro | 33/174 D |

Primary Examiner—Willis Little

Attorney, Agent, or Firm—Larson and Taylor

[57] ABSTRACT

The present invention relates to an apparatus to register the movements of the lower jaw with reference to the skull, substantially comprising an adjustable upper registering yoke anchored to the bridge of the nose and the cheeks with a nasion profile roller for the record plates and the reference indicator on the one hand and the lower registering yoke which is attached by plastering through the intermediary of a spoon to the movable lower jaw on the other hand. The apparatus according to the invention is characterized in that the lower registering yoke exhibits on both side arms which are attached to the cross-bar, holes, into which a recording and measuring device is inserted which is in contact by its registering stylus in the previously determined hinge axis points of the lower jaw either against the left-hand or the right-hand record plate which are attached to the upper registering yoke and permits a continual registration of the movements in all three planes, i.e., a recording of the vertical and horizontal movements and simultaneously the measurement by mechanical, electronic, acoustic or optical means and/or the recording through an auxiliary instrument of the axial displacement of the horizontal movement.

10 Claims, 11 Drawing Figures

U.S. Patent  May 11, 1982  Sheet 1 of 4  4,328,620

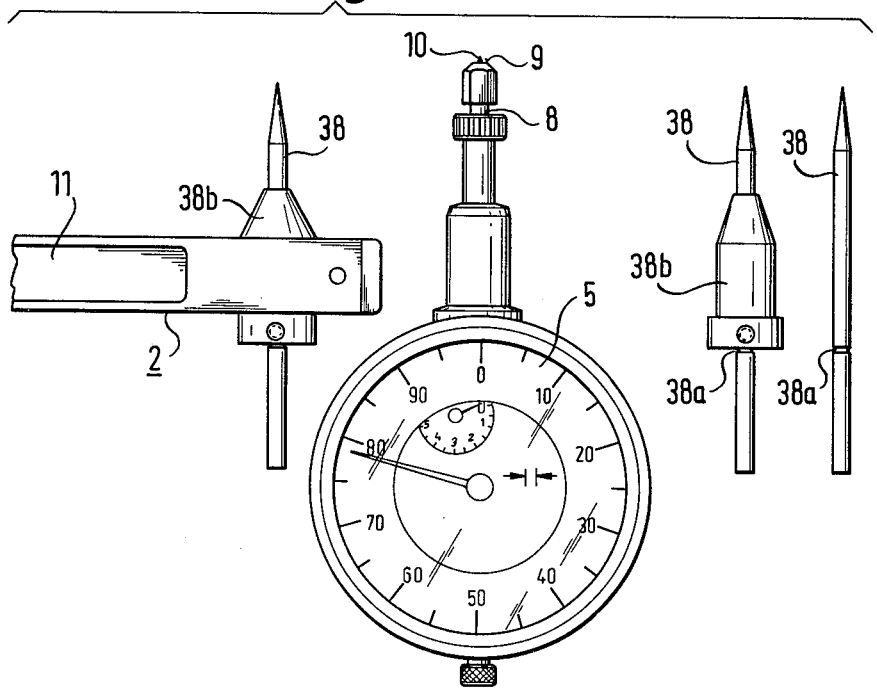
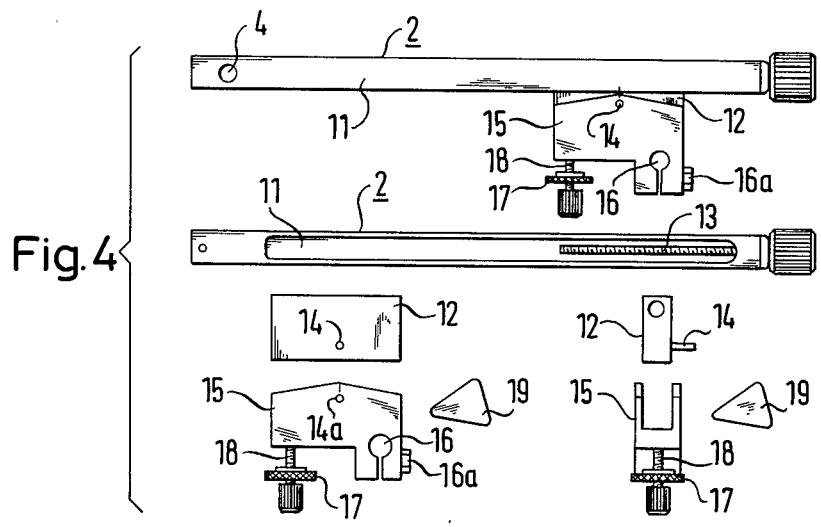

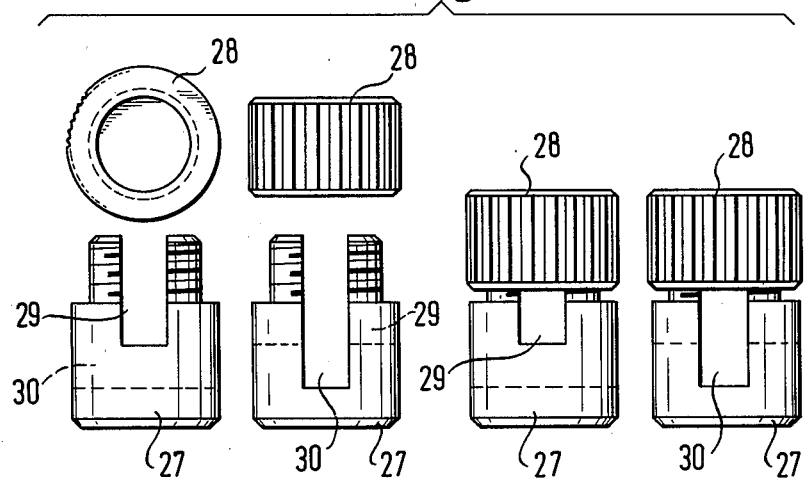
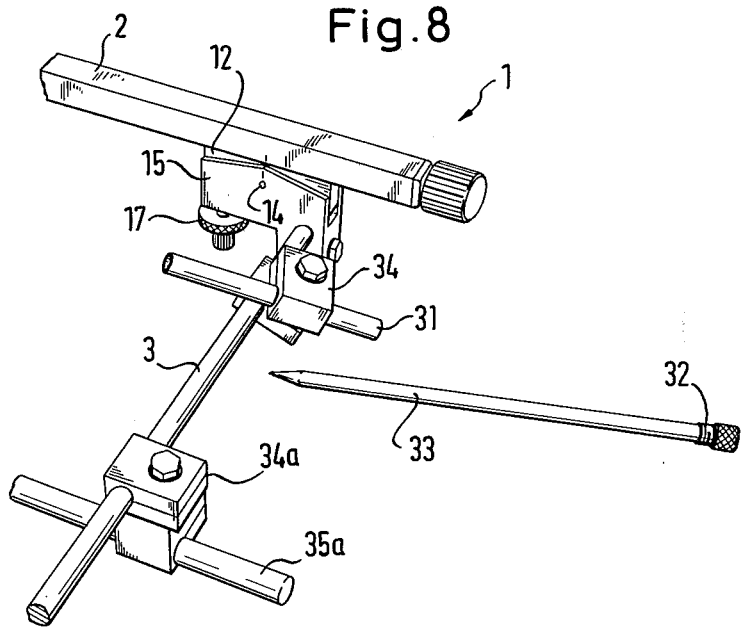

APPARATUS TO REGISTER THE MOVEMENTS OF THE LOWER JAW WITH REFERENCE TO THE SKULL

The present invention relates to an apparatus to register the movements of the lower jaw with reference to the skull, substantially comprising an adjustable upper registering yoke anchored to the bridge of the nose and to the cheeks, with a nasion profile roller for the record plates and the reference indicator on the one hand, and the lower registering yoke, which is attached to the movable lower jaw by means of a spoon or a clamp on the other hand.

In order to achieve this, previously a simultaneous recording was performed on record plates arranged in the various planes. But the pronounced distortions which then resulted from the local positioning of the recording planes and from the telescoping and tilting registering styluses were disadvantageous. Since moreover there was no reference plane on the record plates, a direct interpretation of the lines and the conversion into any desired articulator was therefore impossible. The fact that the evolution of the translatory component could not be detected continuously was also particularly disadvantageous.

It is therefore the aim of the invention to develop an apparatus which permits a continuous measurement of the translatory component with simultaneous recording of the other movement components of the lower jaw and a clear classification of the parameters to the individual positions of the movements. It is also an aim of the invention to conform the apparatus in such a way that the individual parts of the apparatus can be fixed in the respectively desired positions in an easy and accurate manner.

This aim is achieved according to the invention by an apparatus with which it is first of all possible to locate the exit points of the geometrical hinge axis of the lower jaw on the record plates and which then makes it possible, by means of a device which functions simultaneously as a recording and measuring device, to record the vertical and horizontal movements and simultaneously to measure continuously by mechanical, electronic, acoustic or optical means, and/or to record through an auxiliary instrument, the axial displacement of the horizontal movement - i.e. the translatory component.

The object of the invention is thus an apparatus to register the movement of the lower jaw with reference to the skull, substantially comprising an adjustable upper registering yoke anchored to the bridge of the nose and to the cheeks, with a nasion profile roller for the record plates and the reference indicator on the one hand, and the lower registering yoke which is attached to the movable lower jaw by means of a spoon or a clamp on the other hand, which is characterized in that the lower registering yoke exhibits in both side arms which are attached to the cross-bar, holes into which a recording and measuring device is fitted which is in contact by its registering stylus in the previously determined hinge axis point of the lower jaw with either the left-hand or the right-hand record plates which are attached to the upper registering yoke and permits the continuous registration of the movement in all three planes, i.e. the recording of the vertical and horizontal movements and simultaneously the measurement by mechanical, electronic, acoustic or optical means and/or the recording through an auxiliary instrument of the axial displacement of the horizontal movement.

The apparatus according to the invention serves for the diagnosis of the functional process of the jaw articulation system before, during and after therapeutic measures by direct measurement and recording of the horizontal inclinations of the condyle path and of the Bennett values. All articulators adapted to the skull having a definite reference plane can be adjusted precisely on this basis. The recordings of the articular path inclinations and the measurements of the lateral displacement of the lower jaw are made from the same measurement points (the hinge axis points). By virtue of the axial recording in proximity of the joints according to the invention, no serious distortions occur. The recordings of the apparatus according to the invention are therefore directly interpretable and evaluable in contrast to anaxial pantography.

The apparatus according to the invention is simultaneously a hinge axis locator and a transfer instrument.

The upper registering yoke 7 carries the two record plates 6 and the individually adjustable upper reference indicator 22. It is attached to the bridge of the nose, to the cheeks and to the nape of the neck by means of a rubber band.

The lower registering yoke 1 has adjustable side arms 2 for the axle pins 38 or the recording and measuring device 5. It is anchored to the lower jaw by a handled spoon 34, in the case of a toothless jaw the attachment is effected with the mandibular clamp.

After the hinge axle points have been located by the lower registering yoke 1, the axle pins 38 are exchanged for the recording and measuring device with the writing tip 9, 10 and the inclination of the articular path in the case or protrusion and mediofunction is recorded on the record plates provided with millimeter paper.

The determination of the Bennett value is effected by continuous measurement of the lateral displacement (translation). For this the recorded articular path is explored in millimeter steps and the associated values of the lateral displacement are indicated on the measuring instrument. The measured values found are converted into degrees of angle or read off from a previously prepared table. At the same time the intercondylar interval of the articulator with reference to the record plate interval is allowed for. The degres of angle calculated or obtained from the table can also be used directly for adjusting the articulator. For a graphic representation of the Bennett movement, the data are plotted as co-ordinate points in the right-hand part of the findings sheet. Joining them gives the enlarged curve which can be used for scanning with the copying cutter.

In the mechanical version the values for the condyle path inclinations are read off by means of a measuring lens after the reference plane has been drawn in.

Elementary protection applies to the preferred embodiments stated hereinbelow, since these embodiments can also be applied to other corresponding apparatus.

The recording and measuring device is preferably a linear dial gauge, the mechanically operating linear gauge of which functions simultaneously as a pencil, because it exhibits an adjustable pencil lead in a bracket at its tip. The bracket and the pencil lead are arranged similarly as in a compass. It is obviously possible to use as a recording and measuring instrument, instead of the linear dial gauge, other instruments which are based on electronic, acoustic or optical features.

According to a preferred embodiment of the invention, arms slidable in the longitudinal direction and adjustable in their angle of inclination are present at a right angle on the cross-bar of the lower registering yoke, being constructed as slide rails in the form of open or partly open profile tubes of preferably square cross-section and are arranged slidably in the longitudinal direction by means of a spindle on a rocker element, whilst the rocker element is connected by an axle to the rocker bracket fixed to the cross-bar, which exhibits for the adjustment of the angle of inclination, instead of two lockable levelling screws, only one levelling screw provided with a check nut and one or more springs acting in counter-action to the levelling screw.

Another important feature is that the upper registering yoke, which is constituted by the cross-bar and the side arms arranged slidably thereon with the record plates, exhibits on the cross-bar a vertically and horizontally adjustable upper reference indicator, the tip of which is constructed as a ball stud onto which the U-shaped ruler serving to detect the reference plane and provided with a snap device, the lateral arms of which are elastic in the transverse direction, engages. This constitutes an advantage compared to the previously known reference indicators.

The side arms and the cross-bar of the upper registering yoke are preferably connected by means of a novel type of cross clamps, for which protection is therefore claimed also independently of the apparatus according to the invention. The same applies to the upper reference indicator, which is preferably provided with the cross-bar of the upper registering yoke by means of the novel cross clamp. It is particularly advantageous in these cross clamps that they can be locked without a tool. The cross clamps are constituted by a bottom section exhibiting a screw-thread and a top section exhibiting a screw-thread, whilst the bottom section is provided with two incisions of different depths arranged mutually at right angles in order to insert and connect crosswise mutually superposed parts, the contact pressure being obtained by screwing up the top section.

Another interesting innovation according to the invention is a lower reference indicator connected by a screw-thread to a sleeve and attached to the cross-bar of the lower registering yoke by an additional double clamp which surrounds the sleeve. The lower reference indicator can then be removed out of the sleeve after the sleeve has been fixed and the reference points determined, and reinserted again subsequently in the same position, in order to serve to determine the reference point ascertained by the upper reference indicator during the subsequent use of the lower registering yoke as a transfer frame.

Further particulars and features of the invention will emerge from the description hereinbelow in conjunction with the drawing. The drawing, by means of which the invention is further explained, embodies only preferred embodiments of the apparatus according to the invention. The invention itself is therefore not restricted to said preferred embodiments.

FIG. 1 shows the apparatus according to the invention on a patient's head in perspective view. The upper reference frame 7 with its side arms 21, which are mutually connected by means of the cross clamps 24 and 26, are clearly visible. Also visible on the upper registering yoke is the nasion profile roller 36 and the horizontally and vertically adjustable calibrated upper reference indicator 22, likewise attached to the cross-bar 20 by a cross clamp 25. This figure further shows the one record plate 6 on the one side arm of the upper registering yoke, and at the end of the same side arm, the rubber band attached to the side arm, which is passed round the back of the patient's head to the other side arm. In this way the upper registering frame, which is in contact with the nose by means of the nasion roller and with the cheeks, conjointly with the support upon the ears, is given a spectacle-like grip.

This figure also shows clearly the lower registering yoke 1, which is retained by the patient by plastering into the mouth through the intermediary of the spoon 35 which is present on the cross-bar 3. Depending upon the width of the head, the side arms 2 of the lower registering yoke can be adjusted by sliding on the transverse axis 3. The cross-bar 3 then penetrates the rocker bracket, which will be discussed in further detail hereinbelow during the description of FIG. 4. The dial gauge 5 is present at the end of the side arm 2.

Figure 2:
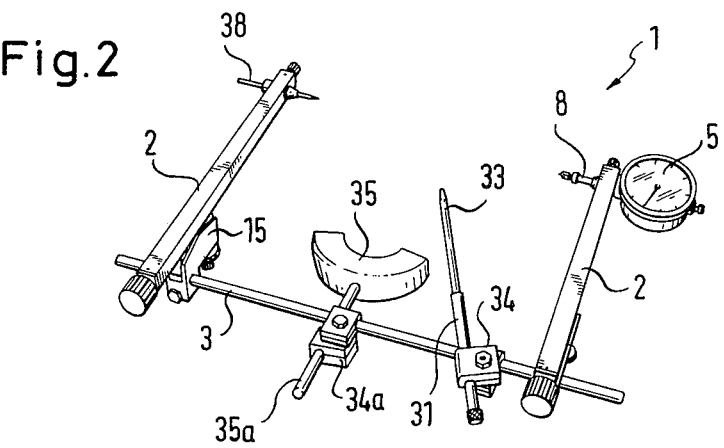
Figure 1A:
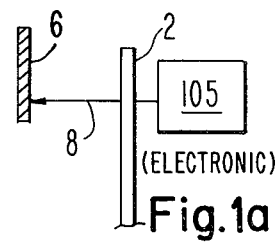
Figure 2A:
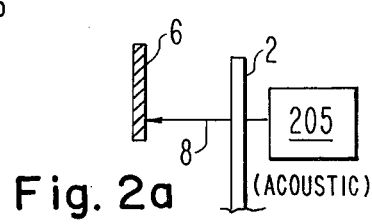
Figure 3A:
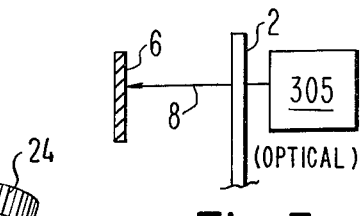

FIGS. 1A, 2A and 3A are diagrammatic views illustrating three modifications of FIG. 1. FIG. 1A illustrates diagrammatically the use of an electronic recording and measuring device 105, FIG. 2A illustrates diagrammatically the use of an acoustic recording and measuring device 205 and FIG. 3A illustrates diagrammatically the use of an optical recording and measuring device 305.

FIG. 2 shows in separate form the lower registering yoke 1 comprising the side arms 2 and the cross-bar 3, the spoon 35, the linear dial gauge 5, the axle pin 38 and the lower reference indicator 33 which is screwed into the sleeve 31, which is itself attached to the cross-bar 3 by means of a double clamp 34.

FIG. 3 shows on the left-hand side the one end of the side arm 2 of the lower registering yoke 1, which is constructed as a partially closed slide rail 11, and at the end of which the axle pin 38 is located. Said axle pin 38 can easily be replaced by the linear dial gauge 5, whilst the bushings 38b of the axle pin and of the dial gauge are identically constructed so that the distance to the tip of the axle pin and also the tip of the linear dial gauge after assembly are both at an equal distance from the side arm 2.

FIG. 3 shows on the right-hand side the axle pin 38 present in the bushing 38 b and beside it the axle pin 38 with the notch marking 38a for the pre-adjustment of the standard interval.

FIG. 4 shows on a smaller scale the side arm 2 which exhibits at its end the hole 4 through which either the axle bushing 38b or the linear dial gauge 5 is introduced. The rocker element 12, which is provided with the rocker bracket 15 through the intermediary of the axle 14, is visible at the right-hand part of the side arm. The cross-bar 3 of the lower registering yoke is passed through the hole 16 of the rocker bracket and locked by means of the fixing screw 16a after adjustment. The central part of FIG. 4 shows the side arm 2 in bottom plan, clearly showing its construction as a partially open slide rail, and a spindle 13 to which the rocker element is adjustably attached. The lower part shows in an exploded view the rocker element 12 and the rocker bracket 15. On the rocker element 12 we see the axle 14 which projects into the holes 14a of the rocker bracket.

Figure 5:
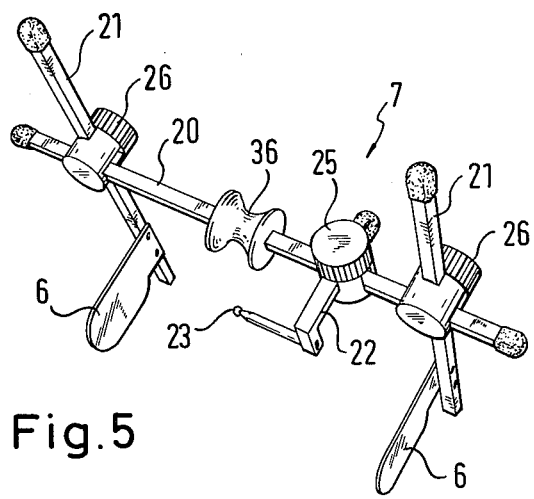

FIG. 5 shows in a separate view the upper registering yoke 7, in which the cross-bar 20 is attached to the side arms 21 by means of the cross clamps 24 and 26. The record plates 6 attached to the two side arms 21 are also visible. Also present on the cross-bar are the nasion profile roller and the upper reference indicator 22 with its tip 23 attached to the cross-bar 20 by means of the cross clamp 25. The embodiment of the upper reference indicator 22 is somewhat differentiated from the embodiment in FIG. 1. This cranked or angled shape has been found particularly successful in practice.

Figure 6:
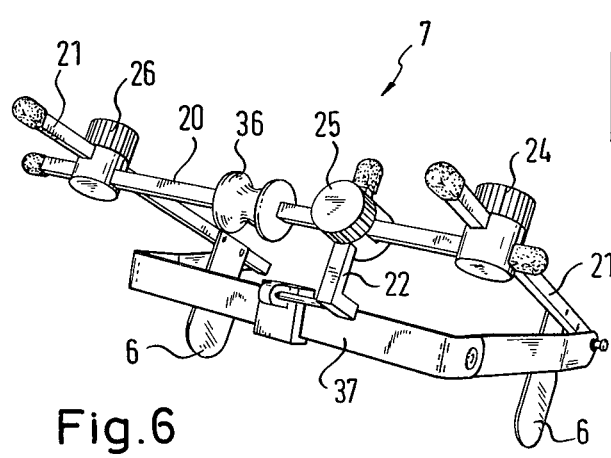

FIG. 6 again shows the upper registering yoke 7 in conjunction with the U-shaped ruler 37 which is attached to the tip of the upper reference indicator 22 by means of ball snaps.

FIG. 7 shows the cross clamps according to the invention with their bottom sections 27 provided with a screw-thread and top sections 28 provided with a screw-thread, which are screwed onto the bottom section. This figure also shows clearly the incisions of different depths in which the cross-bar and the side arm are mounted superposed crosswise.

FIG. 8 shows the lower reference indicator 32 unscrewed out of the sleeve 31, the sleeve 31 of which is fixed by means of the double clamp 34 to the cross-bar 3 of the lower reference yoke.

The operation of the apparatus according to the invention is described hereinbelow.

Instrumentation of the apparatus according to the invention:

1. A strip of soft wax is placed in roof-shaped configuration upon the incisal edges of the lower jaw front teeth. In this way the plaster lining of the spoon 35 is divided into two half shells and can be removed very simply.

2. The spoon 35 with rapid-hardening plaster is inserted distally oriented and the handle is aligned precisely sagittally. Immediate firm biting in the THR (terminal hinge relation=pivot point of hinge axis of lower jaw in the rear position) reduces the vertical obstruction.

3. The upper registering yoke 7 is prepared. The record plates 6 are smeared with vaseline, briefly wiped off before the green record plate label (millimeter paper) is pressed on. The detachment and transfer to the findings card must be effected immediately after the recording.

4. The cross clamps 24, 26 according to the invention are slackened one quarter revolution and the two side arms 21 of the upper registering yoke 7 are set to half length and slid outwards. The upper reference indicator 22 is offset halfway to the side, but the cross clamps 24, 26 are not screwed tight.

5. The nasion profile roller 36 of the upper registering yoke 7 is adapted to the bridge of the nose by rotation and the patient is requested to press upon it with his left index finger. In the case of hypersensitivity a plastic substance is interposed.

6. The operator now stands behind the patient and slides the side arms 21 symmetrically in length and width so that the record plates cover the tragus. The upper registering yoke then sits on the auricular cartilage like spectacles. After the side arms 21 have been drawn towards the nasion profile roller with thumb and index finger, the cross clamps 24, 26 are screwed tight.

7. The rubber band 39 is passed round the back of the head in direct prolongation of the side arms and engaged with moderate tension.

8. The bony rim of the orbita is explored with the round end of the ruler and the upper reference indicator 22 is raised vertically into contact and displaced laterally into contact with the bridge of the nose. The cross clamp 25 is screwed tight. The point of contact of the tip 23 of the upper reference indicator 22 is immediately marked and can be tattooed subsequently.

9. The interval between the inner edges of the side arms 21 is measured and entered into the registration card. The appropriate table for the conversion of the Bennett angle is then selected.

10. The lower registering yoke 1 is prepared:
    (a) The longitudinal adjustments of the side arms 2 are adjusted to the mark line.
    (b) The rocker element 15 with the levelling screws 18 is adjusted horizontally after the check nuts 19 have first been slackened and fully unscrewed.
    (c) The axle pins 38 provided with bushings and the lower reference indicator 33 are left off.
    (d) The fixing of the side arms to the cross-bar 3 is loose, the double clamps 34, 34a are loose.

11. The surplus plaster from the inserted spoon 35 is removed.

12. The cross-bar is attached to the spoon handle by the right-hand double clamp 34a considered from the patient, whilst the two side arms 2 hang downwards. The part of the clamp 34a with the cross-bar 3 is uppermost and aligned in the direction of the lips. After releasing the fixing screws 16a, the side arms 2 are slid inwards and brought into contact with the record plates 6.

13. The patient presses the side arms 2 of the lower registering yoke 1 towards the record plates 6 with his index fingers. Parallelism is thus achieved.

14. The lower jaw is brought into THR (terminal hinge relation or pivot point of hinge axis of lower jaw in the extreme rear position) and the round cross-bar 3 is slid on the spoon handle 35a until the holes for the axle pins 38 provided with the bushes are in the centers of the record plates.

15. The cross-bar 3 of the lower registering yoke 1 is make parallel with the upper registering yoke 7 extremely carefully both in plan and in elevation. Before the double clamp 34a is tightened firmly on the spoon handle 35a, the round cross-bar 3 must be rotated between thumb and index finger in order to compensate the mechanical stresses.

16. The side arms 2 are now slid outwards and hang downwards. The bushings 38b of the axle pins 38 must be inserted accurately to stop and fixed with the screws. The axle pins should be slid out until the notches 30a are just still visible. The side arms are now raised, slid medially to the correct interval of the points of the axle pins 38 and fixed at tragus height. Only the bushings 38b may be screwed firm, not the axle pins 38. The latter should touch the record plates 6 only lightly when the hinge axis is located. The purpose of the notch 38a is to use the measuring instrument subsequently for registration at the correct interval from the record plate 6.

The location of the hinge axes is effected in customary manner by adjusting the side arms 2. The axle pin 38 of the opposite side should then be sufficiently retracted. In order to secure the adjustment the check nuts 17 of the levelling screws 18 are screwed firm and the bushings 38b with the axle pins are then removed. In order to protect the tips of the axle pins 38 when they are put down, they should always be retracted into the bushings 38b and screwed firm.

The recording of the lower jaw movements:

1. The recording and measuring device 5 is prepared by removing the pencil lead bracket with the large knurled screw out of the dial shank by counter-clockwise rotation. The check nut of the collet must be slightly slackened and a lead fed forward or inserted. The point 10 should protrude approximately one millimeter when the collet has been screwed firm again. The writing point is sharpened with the diamond file whilst simultaneously rotating it.

2. The insertion of the recording and measuring instrument is effected in the position of maximum protrusion in order not to cause any undesirable markings in the region of the hinge axis point. For the correct distance of the side arms 2 (axle pin notch 38a) the dial will indicate a positive value (around 1 mm) in THR. The indication can be influenced within limits by varying the depth of insertion.

3. The mandibular is now brought very cautiously into THR and the patient is requested to protrude as far as possible.

4. The mandibular is restored into THR and the lateral excursion path is recorded. For this purpose the request is made to push the chin as far as possible towards the shoulder of the other side. This recording of the lateral articular path may be made guided or unguided. The recording and measuring device is then removed in the limit position.

5. The articular path recording is now protected with a red calibrated adhesive label, of which the first line of the millimeter graduation must be placed very accurately on the hinge axis point. The other graduation lines lie over the path of the mediofunctional movement in order to permit the reading off of the excursion distance in the individual millimeter steps as a distance "s". Each second millimeter step is prolonged.

Bennett measurement:

1. The recording and measuring device 5 is again pushed in up to the stop. In order to assume the THR reliably as starting point, a short forward and backward movement of the lower jaw is executed. The patient should then execute the lateral movement out of the THR in millimeter steps. For this purpose a light controlling guidance by the operator is necessary in order to prevent a protrusive movement of the rotating condylus. This is the more important as the neuromuscular imbalance is greater. The recording and measuring device 5 indicates the lateral displacement of the mandibular which is made of rotation and superimposed translation.

2. The reading off and the entering into the findings sheet commences with the value in THR as initial value (basic or reference value). The indication is then followed in the individual steps and read off e.g. at 1 or 2 etc. mm and entered into the findings sheet. As a comparison, a second test series is optionally performed with a more strongly guided mandibular in the column beneath.

3. When the values for both sides have been entered in the findings sheet (also the side marking L/R and the plate interval) the upper registering yoke 7 can be removed. After sitting the patient upright the points of the axle pins 38 are smeared with paint and slid into contact with the skin both in THR and also at the limit point of the hinge relation. If the two points lie one above the other then the reference point of the hinge axis is also transferable to the skin. A definite marking can be undertaken.

Evaluation:

The evaluation of the articular path inclination commences with the insertion of the U-shaped ruler 37 (reference plane) into the upper registering yoke 7. The ball point 23 of the upper reference indicator 22 engages into the guide block of the U-shaped ruler 37. The universal suspension permits the levelling up of the top edge of the U-shaped ruler 37 to both axis points, the precise contact is fixed with clamps. It is necessary to ensure that the top edge of the U-shaped ruler 37 is in contact with the hinge axis points, since it leads through the center point of the suspension. The axis orbital plane is drawn in with a thin permanent fibre tip pen. Then the labels are immediately removed and placed on the right-hand side of the findings sheet. The angular indications of the articular path inclination are read off directly with the measuring lens and the horizontal condyle path inclination (HCI) for the relevant excursion distance (s) is entered in the findings sheet.

The evaluation of the Bennett angle is commenced by subtracting the initial value (indication of the recording and measuring device 5 in THR) from the individual measured values of the excursion steps. In this way the relative value is obtained, which is entered in the appropriate column of the findings sheet.

The table appropriate to the plate interval is selected. Thus e.g. table 150 is used for a patient width of 146 mm. The intersection of the co-ordinates is the value of the Bennett angle at that point of the excursion. Thus one finds e.g. from table 150 mm, for an excursion distance "s"=4 mm and 0.5 mm a Bennett angle of 8.3 degrees. This value is entered without the decimal place in the "Bennett angle" column.

The graphic plotting of the measurement point on a scale of 10:1 is effected by applying the ruler to the zero point of the millimeter field and to the degree scale at the right-hand edge of the findings sheet. The intersection of the vertical millimeter line with the value of the lateral displacement (offset=$\Delta\eta$) with the line of the degree scale constitutes the measurement point. The connection of the points with the curved ruler represents the curvature of the Bennett guidance. The individual curvature can be copied in the Bennett milling machine.

List of reference numerals

1 Lower registering yoke
2 Side arm of lower registering yoke
3 Cross-bar of lower registering yoke
4 Holes in side arm 2
5 Recording and measuring device
6 Left-hand or right-hand record plate
7 Upper registering yoke
8 Registering stylus of recording and measuring device
9 Point of recording and measuring device
10 Pencil lead
11 Slide rails
12 Rocker element
13 Spindle
14 Axle
14a Holes for axle 14
15 Rocker bracket
16 Hole in rocker bracket
16a Fixing screw
17 Check nut
18 Levelling screw
19 Spring
20 Cross-bar of 7
21 Side arms of 7
22 Upper reference indicator 23 Tip of 22
24 Cross clamp
25 Cross clamp
26 Cross clamp
27 Bottom part of cross clamps
28 Top part of cross clamps
29 Shorter incision in bottom part
30 Longer incision in bottom part
31 Sleeve of 33
32 Screw-thread of 33
33 Lower reference indicator
34 Double clamp
34a Double clamp
35 Spoon
35a Spoon handle
36 Nasion profile roller
37 U-shaped ruler which is mounted on the tip 23 of the upper reference indicator 22.
38 Axle pins
38a Notch in axle pin 38
38b Bushing for axle pin 38

We claim:

1. An apparatus to register the movements of the lower jaw with reference to the skull, substantially comprising an adjustable upper registering yoke having means anchoring the upper yoke to the bridge of the nose and to the cheeks, said means comprising a nasion profile roller, and said upper yoke further having left-hand and right-hand record plates and a reference indicator, and a lower registering yoke which is attached by a plastering through the intermediary of a spoon to the movable lower jaw, said lower registering yoke having a front cross-bar and a pair of side arms, both side arms having holes, a recording and measuring device having a registering stylus being inserted into said holes, into contact against either the said left-hand or the said right-hand record plate at the previously determined hinge axis points of the lower jaw, said device providing continual registration of the movements of the lower jaw in all three planes by recording vertical and horizontal movements thereof, and simultaneously providing movements representing axial displacements of said horizontal movements, and a measuring means responsive to said movements for recording said axial displacement.

2. An apparatus according to claim 1, said measuring means being a mechanical measuring means.

3. An apparatus according to claim 1, said measuring means being an electronic measuring means.

4. An apparatus according to claim 1, said measuring means being an acoustic measuring means.

5. An apparatus according to claim 1, said measuring means being an optical measuring means.

6. An apparatus according to claim 1, wherein the recording and measuring device is a linear dial guage, the mechanically operating linear gauge of which functions simultaneously as a registering stylus, including an adjustable pencil lead in a bracket on its tip.

7. An apparatus according to claim 1, wherein said side arms are slidable along the cross-bar and adjustable in the angle of inclination relative to said cross-bar, said side arms extending at a right angle to the cross-bar at the ends of the cross-bar and being constructed as slide rails in the form of at least partially open profile tubes of generally square cross section, each cross-bar being arranged on a rocker element and slidable in its longitudinal direction by means of a spindle, each rocker element being connected by an axle to a rocker bracket which is attached to the cross-bar, and each rocker bracket including means for adjusting the angle of inclination of its side arm, which means includes a single leveling screw provided with a check nut and including spring means counteracting the levelling screw.

8. An apparatus according to claim 1, wherein the upper registering yoke comprises an upper cross-bar and upper side arms arranged slidably on the upper cross-bar with the said record plates attached thereto, a vertically and horizontally adjustable upper reference indicator on the upper cross bar, the tip of which indicator is constructed as a ball stud onto which is attached a U-shaped ruler, the side arms of said ruler being elastic, and serving to detect the reference plane and being provided with a snap fastener device for connecting the ruler to said indicator.

9. An apparatus according to claim 1, wherein the upper side arms and the upper reference indicator are lockable without a tool on the upper cross bar by means of cross clamps, said cross clamps being constituted by a bottom part having a screw-thread and a top part having a screw-thread, wherein the bottom part is provided with two openings of different depths arranged mutually at right angles to each other in order to insert and connect cross-wise mutually superposed parts, and wherein the contact pressure of the superposed parts is obtained by screwing the top part onto the bottom part.

10. An apparatus according to claim 1, wherein there is provided on the lower cross-bar a lower reference indicator connected by a screw-thread to a sleeve, the sleeve being attached to an additional double clamp on the lower cross-bar, said lower reference indicator being removable from the sleeve after the sleeve has been fastened to the lower cross-bar and the said reference point determined, whereby the lower reference indicator can subsequently be reinserted in the same position, said additional lower reference indicator serving to determine the reference point ascertained with the upper reference indicator when the lower registering yoke is subsequently used as a transfer frame.

* * * * *